United States Patent [19]

Axelrod

[11] 4,390,477

[45] Jun. 28, 1983

[54] DIPHENYL PENTAERYTHRITOL DIPHOSPHONATE

[75] Inventor: Robert J. Axelrod, Glenmont, N.Y.

[73] Assignee: General Electric Company, Pittsfield, Mass.

[21] Appl. No.: 387,500

[22] Filed: Jun. 11, 1982

Related U.S. Application Data

[63] Continuation of Ser. No. 831,056, Sep. 6, 1977, abandoned.

[51] Int. Cl.³ .......................... C08K 5/53; C08F 9/79
[52] U.S. Cl. .............................. 260/927 R; 260/969; 524/120
[58] Field of Search .......................... 260/927 R, 969; 524/120

[56] References Cited

FOREIGN PATENT DOCUMENTS 52-86449  7/1977  Japan ................................. 524/120
1515223  6/1978  Switzerland ....................... 524/120

*Primary Examiner*—John Kight, III
*Assistant Examiner*—Kriellion Morgan
*Attorney, Agent, or Firm*—Hedman, Casella, Gibson, Costigan, & Hoare

[57] ABSTRACT

Flame retardant compositions comprising a polyphenylene ether resin, a styrene resin and a cyclic phosphonate have excellent appearance and physical properties after molding. Especially useful is diphenyl pentaerythritol diphosphonate.

1 Claim, No Drawings

DIPHENYL PENTAERYTHRITOL DIPHOSPHONATE

CROSS-REFERENCE TO RELATED APPLICATION

This is a continuation of Ser. No. 831,056, filed Sept. 6, 1977, now abandoned.

This invention relates to flame retardant thermoplastic compositions, and, more particularly, to compositions comprising a polyphenylene ether resin, a styrene resin, and a cyclic phosphonate.

BACKGROUND OF THE INVENTION

Compositions comprising a polyphenylene ether resin and a styrene resin are well known as useful engineering thermoplastics, for molding, extrusion and the like. They are described in Cizek, U.S. Pat. No. 3,383,435, which is incorporated herein by reference.

Such compositions are normally flammable, particularly if high proportions of styrene resin are present, and aromatic phosphate compounds, e.g., triphenyl phosphate, are used to retard or eliminate flammability. Haaf, U.S. Pat. No. 3,639,506, also incorporated herein by reference, discloses that triphenyl phosphate has a tendency to reduce physical properties and describes the use of combinations of aromatic phosphates and aromatic halogen compounds to flame retard the composition, without markedly lowering resistance to distortion by heat.

Dialkyl pentaerythritol diphosphonates have been reported in Friedman, U.S. Pat. No. 3,141,032, to be generally superior as plasticizers and as flame retardants for synthetic resins. However, it is disclosed that from 10 to 60 parts of the said phosphonate per 100 parts of resin (9.1–37.5 parts per 100 parts of the conbination, by weight) is the proper amount to use, with a stated preference of 30 parts per 100 parts of resin.

It has now been discovered that cyclic phosphonate compounds by themselves are effective nonplasticizing flame retardant additives for the compositions of polyphenylene ethers and styrene resins, at an unexpectedly lower concentration. Moreover, such cyclic phosphonate materials are just as effective in flame retardance in this system is triphenyl phosphate and provide compositions with substantially the same impact resistance as the polymer composition itself.

DESCRIPTION OF THE INVENTION

According to this invention there are provided flame retardant compositions comprising (a) a normally flammable composition comprising a polyphenylene ether resin and a styrene resin, and (b) an effective, flame-retardant amount of a compound of the formula

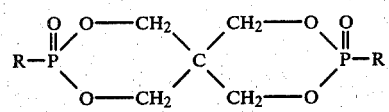

wherein R is alkyl of from 1 to 18 carbon atoms, aryl or alkaryl.

Preferred compositions are those in which the polyphenylene ether resin is of the formula

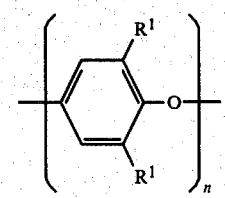

wherein the oxygen ether atom of one unit is connected to the benzene nucleus of the next adjoining unit, n is a positive integer equal to at least 50; and $R^1$, independently, is a monovalent substituent selected from hydrogen, halogen, hydrocarbon radicals free of a tertiary alpha carbon atom, halohydrocarbon radicals having at least two carbon atoms between the halogen atom and the phenyl nucleus and being free of a tertiary alpha carbon atoms, hydrocarbonoxy radicals being free of a tertiary alpha carbon atom, or halohydrocarbonoxy radicals having at least two carbon atoms between the halogen atom and the phenyl nucleus and being free of a tertiary alpha carbon atom.

Especially preferred resins are thos in which $R^1$ is alkyl of from 1 to 6 carbon atoms, especially methyl.

Special mention is made of compositions wherein each $R^1$ is alkyl of from 1 to 6 carbon atoms. The component (a) can be made by those skilled in the art following the teachings of the above-mentioned Cizek patent, and the other references mentioned therein. These materials are also commercially available, e.g., from the General Electric Co., Pittsfield, Mass.

Preferred compositions also include those in which the styrene resin has at least 25 percent by weight units derived from a compound of the formula:

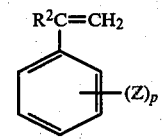

wherein $R^2$ is hydrogen, alkyl of from 1 to 6 carbon atoms or halogen, Z is vinyl, halogen, or lower alkyl, and p is 0 or a whole number equal to the number of replaceable hydrogen atoms in the benzene nucleus. Preferred such styrene resins will be those in which p is O and $R^2$ is hydrogen. Typical styrene resins include, by way of example, homopolymers such as polystyrene and polychlorostyrene, the modified polystyrenes such as rubber modified polystyrenes (high impact polystyrenes), and the styrene containing copolymers, such as the styrene-acrylonitrile copolymers (SAN), styrene-butadiene copolymers, styrene/ethylene-propylene-butadiene terpolymers (EPDM), styrene maleic anhydride copolymers (SMA), styrene-acrylonitrile-alpha-alkyl styrene copolymers, styrene-acrylonitrile-butadene terpolymers (ABS), poly-alpha-methyl styrene, copolymers of ethylvinyl benzene and divinyl benzene, and the like.

The flame retardant cyclic phosphonates will include compounds wherein R is straight or branched-chain alkyl of from about 1 to about 18 carbon atoms, e.g., methyl, ethyl, propyl, i-propyl, n-decyl, hexadecyl, octadecyl, and the like, aryl, e.g., phenyl, naphthyl, and the like, or alkaryl, e.g., benzyl, phenethyl, and the like, containing up to about 18 carbon atoms Preferably, in the cyclic phosphonate, R will be methyl, decyl and, especially preferably phenyl.

The cyclic phosphonates can be made by those skilled in the art, e.g., by following the procedure hereinafter, or in U.S. Pat. No. 3,141,032, for example, which is incorporated herein by reference.

The manner of adding the flame retardant component (b) to the composition (a) is not critical. Preferably, however, such component is added as part of a blend premix, the latter being passed through an extruder with extrusion temperature being maintained between about 450° and 640° F. depending on the composition. The strands emerging from the extruder may be cooled, chopped into pellets, molded to a desired shape.

The concentration of the flame retardant additive (b) can vary, but is dependent to a large extent on the concentration of the styrene resin and the particular styrene resin used. Lower concentrations of styrene resin or less flammable styrene resins require a lower concentration of flame retardant. Moreover, cyclic phosphontes which higher contents of phosphorous can be used in lower amounts. In general, however, amounts of from about 1 to about 10 parts by weight of component (b) can be used. However, to secure the major advantages, only from about 2 to about 10 parts per 100 parts by weight of (a) and (b) combined will be used.

Conventional additives, e.g., reinforcements, pigments, stabilizers, lubricants, and the like can also be included in conventional amounts.

DESCRIPTION OF THE PREFERRED EMBODIMENTS

The following examples illustrate the present invention. In each report, flame retardant properties are determined following procedures established by the Underwriters' Laboratory Bulletin, No. 94. To meet a V-1 rating, bars measuring $2\frac{1}{2}" \times \frac{1}{2}" \times \frac{1}{8}"$ thick are twice ignited for 10 seconds each time. The compositions shall:

A. Not have any specimens which burn with flaming combustion for more than 30 seconds after each application of the test flame.

B. Not have a total flaming combustion time exceeding 250 seconds for the 10 flame applications for each set of 5 specimens.

C. Not have any specimens which burn with flaming or glowing combustion up to the holding clamp.

D. Not have any specimens which drip flaming particles that ignite the dry absorbent surgical cotton located 12 inches (305 mm) below the test specimen.

E. Not have any specimens with glowing combustion which persists beyond 60 seconds after the second removal of the test flame.

EXAMPLES 1-3

Compositions comprising polyphenylene ether resin, polystyrene resin and a cyclic phosphonate of the formula $$R-P \begin{matrix} O \\ \parallel \end{matrix} \begin{matrix} O-CH_2 \\ O-CH_2 \end{matrix} C \begin{matrix} CH_2-O \\ CH_2-O \end{matrix} \begin{matrix} O \\ \parallel \end{matrix} P-R$$

are preblended, extruded at 530° F. and chopped into molding granules. The granules are injection molded at 500° F. (cylinder) and 180° F. (mold) in a 3 oz. Newbury injection molding machine. Physical properties and burn test results for these and for comparison examples are set forth in the Table:

TABLE
Compositions Comprising Polyphenylene Ether, Styrene Resin And Cyclic Phosphonate.

| Example | 1 | 2 | 3 | 3A* | 3B* |
|---|---|---|---|---|---|
| Compositions (pts. per hundred wt.) | | | | | |
| Poly(2,6-dimethyl-1,4-phenylene)ether[a] | 35 | 35 | 35 | 35 | 35 |
| Polystyrene resin[b] | 65 | 65 | 65 | 65 | 65 |
| Cyclic phosphonate | | | | | |
| R = CH$_3$[c] | 2.5 | — | — | — | — |
| R = C$_{10}$H$_{21}$[d] | — | 5.5 | — | — | — |
| R = C$_6$H$_5$[e] | — | — | 4.1 | — | — |
| Triphenyl phosphate[f] | — | — | — | 7.0 | — |
| Properties | | | | | |
| Heat Distortion temp. at 266 psi, °F. | 240 | 232 | 238 | 201 | 228 |
| Izod impact, ft.-lbs./in. notch | 4.1 | — | 4.3 | 4.6 | 3.6 |
| Gardner impact, in.-lbs. | — | 90 | 170 | 170 | 110 |
| Melt viscosity at 1,500 sec. | 1630 | 1400 | — | — | 1550 |
| UL 94 Rating | V-1 | V-1 | V-1 | V-1 | Burns |

*Control
[a] PPO, General Electric Co.
[b] FG 834 rubber modified polystyrene, Foster Grant Co.
[c] Sample from Weston Chemical Corp.
[d] See U.S. Pat. No. 3,141,032
[e] See procedure herein
[f] Conventional, platicizing flame retardant agent.

EXAMPLE 4

Phenyl phosphonic dichloride, 116.95 g is added to a suspension of 40.85 g of pentaerythritol in 400 ml of acetone/triethylamine, cooled to 0°-5° C. The addition is fast enough to maintain the reaction temperature below 10° C. The thick mass was stirred and allowed to warm to 25° C. during 15-20 minutes, then refluxed for 13 hours, cooled, filtered and the cake was sucked dry. Then a product is obtained in 69.3% yield, m.p., after recrystallization of 268°-270° C. The product has an analysis corresponding to the formula:

$$C_6H_5-P \begin{matrix} O \\ \parallel \end{matrix} \begin{matrix} O-CH_2 \\ O-CH_2 \end{matrix} C \begin{matrix} CH_2-O \\ CH_2-O \end{matrix} \begin{matrix} O \\ \parallel \end{matrix} P-C_6H_5$$

Corresponding materials can be prepared by following the procedures of U.S. Pat. No. 3,141,032.

Many variations will suggest themselves to those skilled in this art in the light of the above-detailed description. All such obvious variations are within the full intended scope of the invention as defined by the appended claims.

I claim:
1. A compound of the formula

$$C_6H_5-P \begin{matrix} O \\ \parallel \end{matrix} \begin{matrix} O-CH_2 \\ O-CH_2 \end{matrix} C \begin{matrix} CH_2-O \\ CH_2-O \end{matrix} \begin{matrix} O \\ \parallel \end{matrix} P-C_6H_5$$

* * * * *